(12) United States Patent
Abdel-Magid et al.

(10) Patent No.: US 8,217,142 B2
(45) Date of Patent: *Jul. 10, 2012

(54) LIQUID PHASE PEPTIDE SYNTHESIS OF KL-4 PULMONARY SURFACTANT

(75) Inventors: Ahmed F. Abdel-Magid, Lansdale, PA (US); Urs Eggmann, Fluringen (CH); Cynthia Anne Maryanoff, New Hope, PA (US); Adrian Thaler, Stetten (CH); Frank J. Villani, Perkasie, PA (US)

(73) Assignee: Ortho Pharmaceutical Corporation, Raritan, NJ (US)

( * ) Notice: Subject to any disclaimer, the term of this patent is extended or adjusted under 35 U.S.C. 154(b) by 68 days.

This patent is subject to a terminal disclaimer.

(21) Appl. No.: 12/241,171

(22) Filed: Sep. 30, 2008

(65) Prior Publication Data

US 2009/0259021 A1 Oct. 15, 2009

Related U.S. Application Data

(60) Continuation of application No. 11/581,925, filed on Oct. 17, 2006, now abandoned, which is a continuation of application No. 10/156,882, filed on May 29, 2002, now abandoned, which is a division of application No. 09/436,584, filed on Nov. 9, 1999, now Pat. No. 6,492,490, which is a division of application No. 08/881,971, filed on Jun. 25, 1997, now Pat. No. 6,013,764.

(60) Provisional application No. 60/021,455, filed on Jul. 17, 1996.

(51) Int. Cl.
*C07K 1/06* (2006.01)
*C07K 1/02* (2006.01)

(52) U.S. Cl. ........ 530/335; 530/324; 530/325; 530/326; 530/327; 530/328; 530/329; 530/330; 530/331; 530/333; 530/338

(58) Field of Classification Search .................. None
See application file for complete search history.

(56) References Cited

U.S. PATENT DOCUMENTS

| 4,256,757 A | 3/1981 | Hayashi et al. |
|---|---|---|
| 4,430,262 A | 2/1984 | Engels et al. |
| 4,581,168 A | 4/1986 | Diaz et al. |
| 4,603,209 A | 7/1986 | Tsien et al. |
| 4,607,030 A | 8/1986 | Englert et al. |
| 4,863,963 A | 9/1989 | Nakai et al. |
| 5,164,369 A | 11/1992 | Cochrane et al. |
| 5,260,273 A | 11/1993 | Cochrane et al. |
| 5,407,914 A | 4/1995 | Cochrane et al. |
| 5,599,926 A | 2/1997 | Still et al. |
| 6,013,764 A | 1/2000 | Abdel-Magid et al. |
| 6,492,490 B1 | 12/2002 | Abdel-Magid et al. |

FOREIGN PATENT DOCUMENTS

| WO | WO 92/22315 | 12/1992 |
|---|---|---|
| WO | WO 93/21221 | 10/1993 |

OTHER PUBLICATIONS

Reddy et al. "Circular Dichroism Studies on Synthetic Signal Peptides Indicate beta-Conformationa s a Common Structural Featurei n Highly Hydrophobic Environment*." The Journalof Biological Chemistry, vol. 264, No. 28, Issue of Oct. 5, pp. 16591-16597. 1989.*
Andersson, L. et al., "Large-Scale Synthesis of Peptides," Biopolymers (Peptide Science), vol. 55, No. 3, pp. 227-250, 2000.*
Carey, F.A., Organic Chemistry, McGraw-Hill, New York, 1987, pp. 793-798.
Egboh, H.S., et al., "Synthesis and Characterization of Some Polyurethane Ionomers", Polymer, Jul. 1982, pp. 1167-1171, vol. 23.
Lloyd-Williams, P. et al, "Convergent Solid-Phase Peptide Synthesis", Tetrahedron 49(48), 1993, pp. 11065 and 11087-11089.
Rosario-Jansen, T. et al, "Phospholipids Chiral at Phosphorus: Synthesis of Dioteoylthiophosphatidylcholine and Stereospecificity of Lecithin-Cholesterol Acyltransferase", Biorganic Chemistry 1990, pp. 179-184, vol. 18.
Suehiro, M. et al., "An Improved Method for the Synthesis of Radiolabeled MCN5652 Via Thioester Precursors", Nucl. Med. Biol., 1995, pp. 543-545, vol. 22, No. 4.
International Search Report for application No. PCT/US97/12163 dated Dec. 19, 1997.

* cited by examiner

*Primary Examiner* — Anish Gupta

(57) ABSTRACT

The invention relates to improved liquid phase processes for the preparation of the 21 residue protein component, (Lys-Leu$_4$)$_4$-Lys, of the pulmonary surfactant KL-4. These process are amenable to large scale synthesis and one process employs a method of saponifying an ester which reduces the inherent racemization of the α-carbon.

2 Claims, No Drawings

LIQUID PHASE PEPTIDE SYNTHESIS OF KL-4 PULMONARY SURFACTANT

This application is a continuation of application Ser. No. 11/581,925 filed Oct. 17, 2006, now abandoned, which is a continuation of application Ser. No. 10/156,882 filed May 29, 2002, now abandoned, which is a divisional of Ser. No. 09/436,584 filed Nov. 9, 1999, now U.S. Pat. No. 6,492,490, which is a divisional of U.S. Ser. No. 08/881,971 filed Jun. 25, 1997, now U.S. Pat. No. 6,013,764, which in turn claims the benefit of U.S. provisional application Ser. No. 60/021,455 filed Jul. 17, 1996. The complete disclosures of the aforementioned related U.S. applications are hereby incorporated herein by reference for all purposes.

FIELD OF THE INVENTION

The present invention relates to the field of peptide syntheses and intermediates useful therein. More particularly, the invention relates to the synthesis of the polypeptide component of KL-4, a synthetic pulmonary surfactant.

BACKGROUND

The epithelium of mammalian lungs are lined with an endogenous pulmonary surfactant (PS) which facilitates breathing by aiding the transport of oxygen across the lung air-liquid interface. A deficiency in this surfactant is the primary cause of neonatal respiratory distress syndrome (RDS) and is linked to RDS in adults as well. Native PS is a mixture of lipids and proteins, and although its exact composition is unknown, researchers have prepared a number of exogenous surfactants which are useful in the treatment of RDS in pre-term infants. KL-4 is an example of an exogenous surfactant which is useful in the treatment of RDS as disclosed in U.S. Pat. Nos. 5,164,273, 5,260,273 and 5,407,914, hereby incorporated by reference.

KL-4 is a mixture of a pharmaceutically acceptable phospholipid and a 21 residue polypeptide, (L-lysine-(L-leucine)$_4$)$_4$L-lysine. (SEQ. ID No. 1) As disclosed in the aforementioned patents, this peptide was prepared by solid phase synthesis and recombinant DNA techniques. The solid phase synthesis comprises sequential addition of one or more amino acid residues coupled with suitable protection of amino or carboxyl groups. Although this process is effective, it is not amenable to the large scale synthesis necessary to manufacture a drug substance.

The object of the present invention is the production of the peptide component of KL$_4$, namely (Lys-Leu$_4$)$_4$Lys (SEQ. ID No. 1) by a liquid phase peptide synthesis ("LPPS"). Unlike the methods disclosed in the aforementioned patents, this process is amenable to large scale synthesis.

An additional embodiment of the invention concerns the deprotection of the carboxy terminus of a peptide which was protected as an ester. Most peptide syntheses require manipulation of carboxyl and amino protecting groups. Typically, terminal carboxyl groups are protected as their ester derivative. However deprotection methods may be accompanied by racemization of the α-carbon; a problem that is compounded as the length of the peptide increases. In several steps of the synthesis of (Lys-Leu$_4$)$_4$Lys, an ester protected carboxl group is deprotected. As with most biomimetic products, the configuration of the peptide is crucial and the active configuration of the residues of (Lys-Leu$_4$)$_4$Lys is "L". This invention discloses a method of deprotecting a peptide's ester protected carboxyl group which reduces the amount of racemized product. Although this method is applied in the synthesis of (Lys-Leu$_4$)$_4$Lys, it may be used in the synthesis of other peptides as illustrated hereinafter.

SUMMARY OF THE INVENTION

The invention relates to improved LPPS processes for the preparation of the 21 residue protein component of the pulmonary surfactant, KL-4, which is amenable to large scale synthesis. The first method uses three peptide fragments:

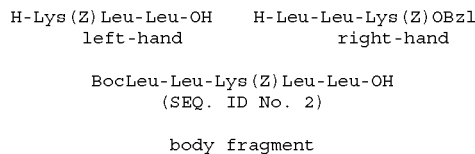

```
H-Lys(Z)Leu-Leu-OH      H-Leu-Leu-Lys(Z)OBzl
    left-hand               right-hand BocLeu-Leu-Lys(Z)Leu-Leu-OH
                (SEQ. ID No. 2)

body fragment
```

The process starts off with a 3-residue right hand fragment which is successively reacted with the 5-residue body fragment to build an 18-amino acid fragment of the formula H-Leu-Leu-(Lys(Z)-Leu$_4$)$_3$-Lys(Z)—OBzl (SEQ. ID No. 3). This 18-amino acid fragment is then reacted with the 3-residue right hand fragment to form the final 21 residue protein of the present invention.

In the second method, a convergent synthesis is employed in which an 8-residue protected polypeptide of the formula: Boc-Lys(Z)-Leu-Leu-Leu-Leu-Lys(Z)-Leu-Leu-OR (SEQ. ID No. 4) is prepared and saponified with tetraalkylammonium hydroxide. The saponified peptide is then reacted with a 13-residue peptide of the formula H-Leu-Leu-(Lys(Z)-Leu$_4$)$_2$-Lys-OBzl (SEQ. ID No. 5) to yield the protected 21-amino acid peptide. Removal of the protecting group by reaction with a suitable acid yields the final KL-4 polypeptide. This convergent method exhibits certain advantages in solubility and control over unwanted by-products, which makes the method particularly suitable to large scale synthesis.

In another aspect of the present invention is a novel method for the deprotection of the carboxy terminus of a peptide protected as an ester. This method comprises saponifying the protected peptide with tetraalkylammonium hydroxide reagent in a suitable solvent. This process provides a method of deprotecting the peptide which reduces the amount of racemization at the α-carbon.

DETAILED DESCRIPTION OF THE INVENTION

Herein, the amino acid nomenclature corresponds to standard conventions where: L-leucine is "L" or "Leu", L-lysine is "K" or "Lys", L-alanine is "A" or "Ala", benzyloxycarbonyl is "Z" or CBZ, D-(1-naphthyl)alanine is "D-Nal", 4-chlorophenylalanine is "D-Cal", L-serine is "L-Ser" and D-3-pyridylalanine is "D-Pal". In addition all amino acid residue sequences are represented by formulae whose left to right orientation is in the conventional direction of amino-terminus to carboxy-terminus. A dash at the beginning or end of the sequence indicates a bond to a radical such as H, OH or OBzl; and a dash in the middle of the sequence indicates a convential amide bond. Other abbreviations and symbols are as follows: DMF is N,N-dimethylformamide, MeOH is methanol, HOBT is 1-hydroxybenzotriazole, THF is tetrahydrofuran, DCC is 1,3 dicyclohexylcarbodiimide, EtOH is ethanol, iPrOH is isopropanol, HBTU is N,N,N'-tetramethyl-O-(1H-benzotriazol-1-yl)uronium-hexafluorophosphate), DIPEA is N,N-diisopropylethylamine, NMP is 1-methyl-2-pyrrolidone, HOOBT is 3,4-dihydro-3-hydroxy-4-oxo-1,2,3- benzotriazine, WSCDI (water soluble carbodiimide) is 1-(dimethylaminopropyl)-3-ethylcarbodiimide hydrochloride and DIC is 1,3-diisopropylcarbodiimide. The term "alkyl" includes straight and branched groups; the term "hydroxide" includes Group I metal hydroxides (NaOH, LiOH and the like) as well as tetraalkylammonium hydroxides; the term "salts" includes tetraalkylammonium halides and tetrahalo borates and "Ac" is acetyl.

The synthesis of (Lys-Leu$_4$)$_4$Lys (SEQ. ID No. 1) in accordance with the present invention, follows two pathways. Procedure A uses three peptides fragments: a 3-residue left-hand (amino-end), a three residue right hand (carboxy terminus) and a five residue body fragment to construct the molecule.

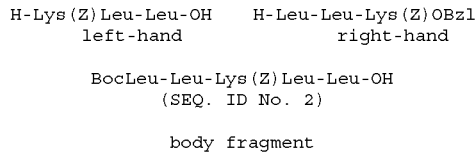

body fragment

As illustrated in Scheme A, H-Leu-Leu-Lys(Z)—OBzl and Boc-Leu-Leu-Lys(Z)-Leu-Leu-OH (SEQ. ID No. 2) are reacted together in the presence of a peptide coupling agent and an inert solvent at about 0° C. to room temperature to give Boc-Leu-Leu-Lys(Z)-Leu-Leu-Leu-Leu-Lys(Z)—OBzl. (SEQ. ID No. 6) Examples of suitable peptide coupling agents include: DCC, DIC, HBTU, WSCDI, HOBT, HOOBt, where the preferred agents are HOOBT and HTBU. Solvents are chosen for their compatibility with the chosen coupling agent. Suitable solvents include DMF, THF, NMP and acetonitrile, where a mixture of DMF and acetonitrile is preferred. If the acid salt of H-Leu-Leu-Lys(Z)—OBzl is used, this peptide is neutralized with an organic base. The Boc protecting group is cleaved by treating Boc-Leu-Leu-Lys(Z)-Leu-Leu-Leu-Leu-Lys(Z)—OBzl (SEQ. ID No. 6) with an acid at about −20 to 0° C. under an inert atmosphere. Although a solvent may be used with a gaseous acid, such as HCl, the preferred method uses neat trifluoroacetic acid at about 0° C.

H-Leu-Leu-Lys(Z)-Leu$_4$-Lys(Z)—OBzl (SEQ. ID No. 6) is treated with a peptide coupling agent, an organic base and Boc-Leu-Leu-Lys(Z)-Leu-Leu-OH (SEQ. ID No. 2) in an inert solvent at about −4 to 10° C. to give Boc-Leu-Leu-(Lys(Z))$_2$-Lys(Z)—OBzl. (SEQ. ID No. 5) The preferred peptide coupling agents are HOOBT and HBTU, the preferred solvent is DMF and the preferred organic base is DIPEA. The Boc protecting group is cleaved by treating Boc-Leu-Leu-(Lys(Z)-Leu$_4$)$_2$-Lys(Z)—OBzl (SEQ. ID No. 5) with an acid at about −20 to 0 C. under an inert atmosphere. The preferred acid was HCl and the inert solvent was ethyl acetate.

H-Leu-Leu-(Lys(Z)-Leu$_4$)$_2$-Lys(Z)—OBzl (SEQ. ID No. 5) is treated with a peptide coupling agent, an organic base and Boc-Leu-Leu-Lys(Z)-Leu-Leu-OH (SEQ. ID No. 2) in an inert solvent at about −4 to 10° C. to give Boc-Leu-Leu-(Lys(Z)-Leu$_4$)$_3$-Lys(Z)—OBzl. (SEQ. ID No. 3) The preferred peptide coupling agents are HOOBT and DIC, the preferred solvent is THF and the preferred organic base is DIPEA. The Boc protecting group is cleaved by treating Boc-Leu-Leu-(Lys(Z)-Leu$_4$)$_3$-Lys(Z)—OBzl (SEQ. ID No. 3) with an acid at about −20 to 0° C. under an inert atmosphere.

H-Leu-Leu-(Lys(Z)-Leu$_4$)$_3$-Lys(Z)—OBzl (SEQ. ID No. 3) was treated with a salt, an organic base, a peptide coupling agent, water and Z-Lys(Z)-Leu-Leu-OH in an inert solvent at about 0 to 20° C. over 2 to 5 h to give Z-(Lys(Z)-Leu$_4$)$_4$-Lys (Z)—OBzl. (SEQ. ID No. 1) The preferred coupling agents are DIC and HOOBT, the preferred solvent is THF and the preferred salt is LiBF$_4$. The benzyl protecting groups are removed by hydrogenating Z-(Lys(Z)-Leu$_4$)$_4$-Lys(Z)—OBzl (SEQ. ID No. 1) in the presence of a catalyst and an inert solvent under a positive H$_2$ atmosphere. The preferred catalyst is Pd/C, the preferred solvent is acetic acid and the preferred H$_2$ pressure is 2 to 2.2 bar.

Scheme A

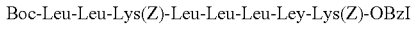

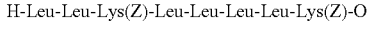

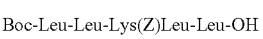

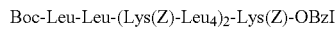

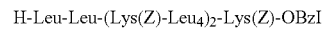

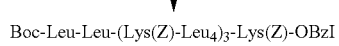

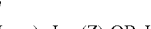

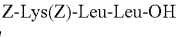

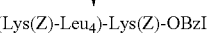

Procedure B follows another approach. This method employs a convergent pathway where two larger fragments are combined to produce the protected final product. In addition this method uses tetrabutylammonium hydroxide to saponify an ester protected carboxy group with less than 1% racemization of the α-carbon.

As illustrated by Scheme B, H-Leu-Leu-Lys(Z)-Leu-Leu-OR (SEQ. ID No. 2) is treated with Boc-Lys(Z)-Leu-Leu-OH, a peptide coupling agent, an organic amine in an inert solvent at about −5 to −2° C. for about 2 to 3 h to give Boc-Lys(Z)-Leu-Leu-Leu-Leu-Lys(Z)-Leu-Leu-OR. (SEQ. ID No. 4) The preferred coupling agents are HOOBT and HBTU, the preferred organic base is DIPEA, the preferred solvent is DMF and the preferred group for R is methyl. The terminal ester protecting group is saponified by treating Boc-Lys(Z)-Leu-Leu-Leu-Leu-Lys(Z)-Leu-Leu-OR (SEQ. ID No. 4) with a tetraalkylammonium hydroxide and water in an inert organic solvent at about −17 to 0° C. over 10 to 160 min. Inert solvents include DMF and THF, tetraalkylammonium hydroxide reagents include tetrabutylammonium hydroxide, tetramethylammonium hydroxide, tetraethylammonium hydroxide and tetrabenzylammonium hydroxide. The preferred solvent is THF, the preferred tetraalkylammonium hydroxide is tetrabutylammonium hydroxide and the preferred temperature is −5 to 0° C. The reaction should be monitored by analytical methods, particularly HPLC in order to determine when the starting ester is saponified, for racemization increases over time.

Boc-(Lys(Z)-Leu$_4$)Lys(Z)-Leu-Leu-OH (SEQ. ID No. 4) is treated with a salt, a peptide coupling agent, an organic base and H-Leu-Leu-(Lys(Z)Leu$_4$)$_2$-Lys-OBzl (SEQ. ID No. 5) in an inert organic solvent at about 0 to 25° C. over 1 to 30 h to give Boc-(Lys(Z)-Leu$_4$)$_4$Lys(Z)—OBzl. (SEQ. ID No. 1) The preferred coupling agents are HOOBT and DIC, the preferred organic base is DIPEA, the preferred solvent is THF/water and the preferred salt is tetrabutylammonium chloride.

The protecting groups of Boc-(Lys(Z)-Leu$_4$)$_4$Lys(Z)—OBzl (SEQ. ID No. 1) are removed by treatment with trifluoroacetic acid followed by hydrogenation in the presence of a catalyst and an inert solvent under a positive H$_2$ atmosphere. The preferred catalyst is Pd/C, the preferred solvent is acetic acid and the preferred H$_2$ pressure is 2 to 2.2 bar.

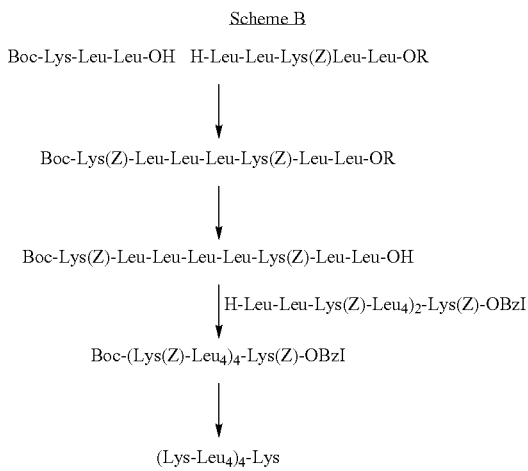

Scheme B

Although tetraalkylammonium hydroxides are employed in the synthesis of (Lys-Leu$_4$)$_4$-Lys, (SEQ. ID No. 1) their utility is not restricted to the saponification of peptides with L-confirmations, nor to peptides of Lys or Leu. It is used in the saponification of Ac-D-Nal-D-p-Cal-OMe, where this peptide was treated with tetraalkylammonium hydroxide in an inert solvent at about −10 to 0° C. to give Ac-D-Nal-D-p-Cal-OH. The preferred tetraalkylammonium hydroxide is tetrabutylammonium hydroxide and the preferred solvents are DMF and THF. This procedure gives 2.6% of the undesired L isomer while other methods, namely NaOH and aqueous acetone give 13% of the undesired diastereomer. In addition, tetraalkylammonium hydroxides are used in the saponification of Ac-D-Nal-D-p-Cal-D-3-Pal-L-Ser (OH)—OBzl. (SEQ. ID No. 7) The preferred solvent for this saponification is THF, the preferred hydroxide is tetrabutylammonium hydroxide and the preferred temperature is about −6 to −3° C.

The following examples are meant to illustrate the invention, not to limit it. Other embodiments will be obvious to those skilled in the art and are claimed by this invention. The identity of the compounds was confirmed by HPLC and LC comparison with known standards. The purity of the compounds was determined by their HPLC area %, where the racemization % was determined by the same method.

EXAMPLE 1

Step 1

Boc-Leu-Leu-OMe

4-Methylmorpholine (12.62 g, 124.8 mmol), Boc-Leucine monohydrate (29.92, 120.0 mmol) and HOBt (1.62 g, 12.0 mmol) were added to a solution of H-Leu-OMe.HCl (21.80 g, 120.0 mmol) in ethyl acetate (205 g). A solution of DCC (29.71 g, 144.0 mmol) in ethyl acetate (25.0 g) was added at 0 to 5° C. over 30 min and the resulting mixture was stirred over 2 h at a maximum temperature of 20° C. The resulting urea was removed by filtration and washed with ethyl acetate and the combined organic filtrate was extracted with successive portions of 5% aq. K$_2$CO$_3$ and 5% aq. KHSO$_4$. The organic layer was dried (MgSO$_4$), concentrated in vacuo, and the residual solid was recrystallized from petroleum ether (bp 100-125° C.) to give Boc-Leu-Leu-OMe (38.6 g, 89.8%).

Step 2

Boc-Leu-Leu-OH

A solution of NaOH (1.34 g, 33.5 mmol) in water (15.0 g) was added dropwise over 10 min to the solution of Boc-Leu-Leu-OMe (10.0 g, 27.9 mmol) in acetone (20.0 g) and water (50.0 g) at 18-22° C. The reaction mixture was stirred at this temperature for 1 h and then analyzed by HPLC. When the methyl ester is under 5%, the reaction stirred for an additional 0.5 h. A white turbidity formed by the end of the reaction which was removed by filtration and rinsed with water (5.0 g). The clear filtrate was treated with formic acid (ca 0.8 g) to form a cloudy solution followed by immediate crystallization of product. Additional formic acid (1.5 g) was added (to pH 4.0-4.5) and the resulting product was collected by filtration then was washed by a mixture of acetone (10.0 g) and water (40.0 g). The solid product was suspended in a mixture of acetone (14.0 g) and water (56.0 g) for 15 min. The solid was collected by filtration and washed with a mixture of acetone (7.5 g) and water (30.0 g) and dried in vacuo at 45° C. Yield: 8.6-8.8 g (89.6-91.7%).

Step 3

H-Leu-Leu-OMe.HCl

Gaseous HCl (10.2 g, 279 mmol) was infused into a mixture of Boc-Leu-Leu-OMe (17.9 g, 50.0 mmol) and ethyl acetate (71.4 g) at 20 to 25° C. After 30 min, t-butyl methyl ether (142.9) was added to the resulting solution followed by a seed crystal. The resulting solid crystalline product was filtered at 0 to 5° C. and dried in vacuo to give H-Leu-Leu-OMe.HCl (14.1 g, 95.7%).

Step 4

Boc-Lys(Z)-Leu-Leu-OMe

Isobutyl chloroformate (13.66 g, 100 mmol) was added dropwise over 15 min at −15 to −10° C. to a solution of Boc-Lys(Z)—OH (38.04 g, 100 mmol) in ethyl acetate (200 g). Another portion of ethyl acetate was added (10 g) and the mixture was stirred for 15 min. 4-Methylmorpholine (10.12 g, 100 mmol) was added dropwise over 15 min at −15 to −10° C., followed by an additional portion of ethyl acetate (10.0 g) and the resulting mixture was stirred for 2 h. In a separate reaction vessel 4-methylmorpholine (10.12 g, 100 mmol) was added dropwise over 15 min, to a solution of H-Leu-Leu-OMe.HCl (29.48 g, 100 mmol) in ethyl acetate (200.0 g) at −23 to −10° C. An additional portion of ethyl acetate (10.0 g) was added followed by the addition of the formed anhydride over 30 to 45 min at a temperature of −8 to −10° C. Another portion of ethyl acetate (30.0 g) was added and the resulting mixture was stirred for 1.5 h. Ethyl acetate (50.00 g) was added, the solution was filtered and the resulting organic filtrate was concentrated in vacuo. The resulting solid was recrystallized from petroleum ether (bp 100 to 125) to give Boc-Lys(Z)-Leu-Leu-OMe (55.9 g, 90.2%).

Step 5

H-Lys(Z)-Leu-Leu-OMe.HCl

A solution of HCl (28 g, 770 mmol) in ethyl acetate (100 g) at −10° C. was rapidly added to Boc-Lys(Z)-Leu-Leu-OMe (35.0 g, 55.74 mmol) under $N_2$ at −15 to −12° C. The mixture was stirred and maintained at −15 to −12° C. for 60 to 70 min and allowed to crystallize for 1 h at −10 to −5° C. The solid was filtered while excluding moisture, washed with several portions of t-butyl methyl ether and dried in vacuo to give H-Lys(Z)-Leu-Leu-OMe.HCl (28.7 g, 91.4%).

Step 6

Boc-Leu-Leu-Lys(Z)-Leu-Leu-OMe     (SEQ. ID No. 2)

4-Methylmorpholine (2.53 g, 25 mmol) was added to a solution of H-Lys(Z)-Leu-Leu-OMe.HCl (13.93 g, 25 mmol) in DMF (85.0 g) at 10° C. HOBt (3.38 g, 25 mmol), Boc-Leu-Leu-OH (8.61 g, 25 mmol) and DIC (3.47 g, 27.5 mmol) were added over 30 min at 8-10° C. An additional portion of DMF (5.0 g) was added and the reaction was kept at 8-10° C. for 16 h. The reaction was stirred at 18-20° C. for 3 h, cooled to 5-10° C. and treated with $H_2O$ (130.0 g). A solid precipitated at 25° C. which was filtered, washed with $H_2O$ and recrystallized from MeOH and $H_2O$ to give Boc-Leu-Leu-Lys(Z)-Leu-Leu-OMe (SEQ. ID No. 2) (18.3 g, 86.4%).

Step 7

Boc-Leu-Leu-Lys(Z)-Leu-Leu-OH     (SEQ. ID No. 2)

A solution of NaOH (1.44 g, 36.0 mmol) in $H_2O$ (15.0 g) was added at 20-25° C. over 5 min to a mixture of Boc-Leu-Leu-Lys(Z)-Leu-Leu-OMe (SEQ. ID No. 2) (12.0 g, 14.16 mmol) THF (48.0 g) and $H_2O$ (18.0 g). The resulting mixture was stirred for 2 h. 98% Formic acid (5 g) was added, followed by ethyl acetate (30.0 g). The resulting organic phase was washed with $H_2O$, concentrated in vacuo and the residue was dissolved in MeOH (60.0 g). The solids were filtered and rinsed with an additional portion of MeOH (8.0 g). The combined MeOH solution was heated to 60-65° C. and $H_2O$ (30.0 g) was added over 10 min. This mixture was cooled to 20-25° C., the solid product began to crystallize. An additional portion of $H_2O$ (35.0 g) was added and the mixture was stirred for 1 h. The solid product was filtered, washed with $H_2O$ and dried in vacuo to give Boc-Leu-Leu-Lys(Z)-Leu-Leu-OH (SEQ. ID No. 2) (11.5 g, 97.5%).

Step 8

Boc-Leu-Leu-Lys(Z)—OBzl

A solution of H-Lys(Z)—OBzl.HCl (20.35 g, 50 mmol) in DMF (50.0 g) was treated with $Et_3N$ (5.26 g, 51 mmol) at 25 to 30° C. Boc-Leu-Leu-OH (17.57 g, 51 mmol) and HOBt (1.08 g, 8 mmol) were added followed by an additional portion of DMF (7.0 g). A solution of DCC (11.35 g, 55 mmol) in DMF (25.0 g) was added dropwise over a period of 30 min at 20° C. The reaction mixture was stirred for 4 h and the temperature was allowed to rise (to ca. 34° C.). Acetic acid (0.2 g) was added, the resulting suspension was filtered and the filter cake was rinsed with DMF (15.0 g). Acetone (126.0 g) was added to the filtrate, followed by two portions of $H_2O$ (66.5 g, 89.5 g-30 min apart). The resulting precipitate was filtered and the filter cake was washed with acetone (53.0 g) and $H_2O$ (212.0 g). The crude solid was triturated with a mixture of acetone (100 g) and $H_2O$ (400 g), filtered, washed with $H_2O$ and dried in vacuo at 40° C. to give Boc-Leu-Leu-Lys(Z)—OBzl (32.6 g, 93.4%).

Step 9

H-Leu-Leu-Lys(Z)—OBzl

A cooled solution (−15° C.) of gaseous HCl (50.0 g, 1.37 mol) in ethyl acetate (250 g) was added to Boc-Leu-Leu-Lys(Z)—OBzl (50.0 g, 71.7 mmol) at −15 to −10° C. over 15 min. The mixture was stirred at −15 to −10° C. for 75 min and t-butyl methyl ether (310 g) was added over 25 min. The temperature was allowed to rise to about −8 to −5° C. and the excess HCl was removed under reduced pressure. Another portion of t-butyl methyl ether (310.0 g) was added over 15 min and the reaction temperature was maintained at −5° C. for approximately 2 h. The resulting solid product, H-Leu-Leu-Lys(Z)—OBzl.HCl was filtered and rinsed with t-butyl methyl ether then dried to give 41.8 g, 92.1%.

Step 10

Z-Lys(Z)-Leu-Leu-OMe

4-Methylmorpholine (1.26 g, 12.5 mmol) and HOBt (1.69 g, 12.5 mmol) were added to a solution of H-Leu-Leu-OMe-.HCl (4.04 g, 13.75 mmol) in ethyl acetate (160.0 g) and DMF (36.0 g) over 15 min. Z-Lys(Z)—OH (5.18 g, 12.5 mmol) was added to this stirred mixture over 15 min. A solution of DCC (3.10 g, 12.5 mmol) in ethyl acetate (10.0 g) was added dropwise at 18-20° C. over 30 min. The reaction mixture was stirred at 18-20° C. for 16 h and filtered. The filter cake was washed with ethyl acetate (100.0 g) and the combined filtrate was washed with aqueous $NaHCO_3$. The resulting organic layer was washed with aqueous NaCl and concentrated under reduced pressure. The residue was dissolved in MeOH (80.0 g) at about 50° C. Water (160 g) was slowly added and the mixture was stirred for about 1 h at 20° C. The resulting solid was filtered, washed with $H_2O$ (80.0 g) and dried at 40° C. in a vacuum oven to give 8.16 g, 99.6% of the product Z-Lys(Z)-Leu-Leu-OMe.

Step 11

Z-Lys(Z)-Leu-Leu-OH

A solution of $LiOH.H_2O$ (7.36 g, 0.182 mol) in $H_2O$ (360 g) was added dropwise over 20 min to a solution of Z-Lys(Z)-

Leu-Leu-OMe (100 g, 0.152 mol) in acetone (40 mL) under N$_2$ at 25° C. The reaction mixture was stirred for an additional 40 min at 25° C. The pH was adjusted to 4, using 96% formic acid (1.25 g, 0.0273 mol). The reaction mixture was cooled to 15° C. and water (42 g) was added dropwise over 1 h followed by a few seed crystals of Z-Lys(Z)-Leu-Leu-OH and the mixture was stirred at 15° C. for 2 h. The resulting solid was collected by filtration and washed with H$_2$O (10 mL) and acetone (10 mL). The solid was air dried then further dried in a vacuum oven at 45° C. for 24 h to give 87.3 g, 89.7% of Z-Lys(Z)-Leu-Leu-OH.

Step 12

Boc-LLK(Z)-LLLLK(Z)-OBzl    (SEQ. ID No. 6)

Boc-Leu-Leu-Lys(Z)-Leu-Leu-OH (SEQ. ID No. 2) (41.65 g, 50 mmol), H-Leu-Leu-Lys(Z)—OBzl.HCl (31.65, 50.0 mmol) HOBt (8.10 g, 60 mmol), and HBTU (22.75, 60 mmol) was dissolved in DMF (200 g) and acetonitrile (300 g) and was cooled to 0° C. DIEA (19.35 g, 150 mmol) was added over 10 min and the resulting mixture was stirred at 0° C. for 2 h. The temperature was allowed to rise to 20° C. and the mixture was stirred for another 1 h. The reaction mixture was poured into water (2500 g) and the resulting solid was collected by filtration and dried in vacuo at 45° C. The crude solid was powdered and stirred with a mixture of acetone (500 g) and t-butyl methyl ether (500 g) for 20 min at 50° C. and for 1.5 h at room temperature. This mixture was filtered and the solid was washed with a mixture of acetone (50 g) and t-butyl methyl ether (50 g) to give Boc-LLK(Z)-LLLLK(Z)—OBzl (SEQ. ID No. 6) (65.6 g, 92.9%).

Step 13

H-LLK(Z)-LLLLK(Z)-OBzl•TFA    (SEQ. ID No. 6)

Trifluoroacetic acid (11 mL) was cooled in an ice bath to 0° C. under N$_2$. Boc-LLK(Z)-LLLLK(Z)—OBzl (SEQ. ID No. 6) (2.5 g, 1.77 mmol) was added in one portion and the mixture stirred at 0° C. for 1 h. The resulting solution was poured into ice water (100 mL) and stirred for 20 min. The resulting white solid was collected by filtration and washed with distilled water (50 mL) then air-dried. Yield of white solid product was 2.49 g (98.8%); HPLC area % purity: 97

Step 14

Boc-LL-K(Z)LLLLK(Z)-LLLLK(Z)-OBzl    (SEQ. ID No. 5)

H-LLK(Z)LLLLK(Z)—OBzl.TFA (SEQ. ID No. 6) (19.4 g, 13.608 mmol) was dissolved in DMF (500 mL) at 50° C. in a 1 L reaction flask. The solution was cooled to –4° C. and stirred under nitrogen. Boc-LLK(Z)LL-OH (SEQ. ID No. 2) (11.60 g, 13.92 mmol) was added and was dissolved immediately. HOBT (4.44 g, 27.216 mmol) and HBTU (6.193 g, 16.3 mmol were added followed by a solution of DIPEA (5.28 g, 40.824 mmol) in DMF (20 mL) at –4° C. over 10 min. The resulting yellow solution was stirred at –4° C. for 4 h (HPLC analysis showed a near complete reaction after 2 h). The reaction mixture was allowed to warm up to 10° C. then was poured into ice water (1 L). Saturated aq. NaCl (100 mL) was added and the mixture stirred for 20 min at rt. The yellow solid was collected by filtration and was washed with distilled water (300 mL) then was air-dried overnight. Yield of crude product (28.9 g). The crude solid was suspended in MeOH (200 mL) where it became sticky. The mixture was heated to boiling on a steam bath; the material solidified as a result of this treatment. The lumpy solid was powdered and heating was continued for additional 10 min. The mixture was allowed to cool to room temperature and the solid was collected by filtration, rinsed with MeOH (50 mL) and dried to give Boc-LL-K(Z)LL*LLK(Z)-LLLLK(Z)—OBzl (SEQ. ID No. 5) (27.9 g, 96.5%), area % HPLC purity: 93.0%, D-13 (*) diastereomer: 0.4%.

Step 15

H-LLK(Z)LLLLK(Z)-LLLLK(Z)-OBzl•HCl    (SEQ. ID No. 5)

Gaseous HCl (98.6 g) was introduced to a suspension of Boc-LLK(Z)LLLLK(Z)-LLLLK(Z)—OBzl (SEQ. ID No. 5) (38.1 g, 17.9 mmol) in ethyl acetate (280 g) at –18 to –22° C. over 80 min. The resulting solution was stirred at –16 to –14° C. for 60 min. The excess HCl was removed under reduced pressure at –20 to –0° C. and diethyl ether (192 g) was added at –3 to 3° C. A solution of potassium bicarbonate (33 g) in H$_2$O (200 g) was added in portions until the pH of the reaction mixture was between 1.5 and 2.5, the resulting mixture was warmed to 19 to 23° C. and stirred for 30 min. The resulting solid was collected by filtration, rinsed with H$_2$O and dried in vacuo at 35 to 40° C. to give H-LLK(Z)LLLLK(Z)-LLLLK(Z)-Obzl.HCl (SEQ. ID No. 5) (34.9 g, 95%).

Step 16

(SEQ. ID No. 3)
Boc-LLK(Z)LLLLK(Z)LLLLK(Z)-LLLLK(Z)-OBzl

H-LLK(Z)LLLLK(Z)-LLLLK(Z)—OBzl (SEQ. ID No. 5) (10.0 g, 4.85 mmol) was added to a stirred solution of LiBF$_4$ (3.04 g, 32.4 mmol) in NMP (99 g) THF (286 g). Boc-Leu-Leu-K(Z)Leu-Leu-OH (5.24 g, 6.29 mmol) was added and the mixture was homogenized until a viscous gel was formed. Water (36 g) was added and the mixture was stirred for 20 min a well stirred turbid solution is obtained. The reaction mixture was cooled to –6 to –4° C. and treated with HOOBt (2.76 g, 16.92 mmol) and DIC (1.84 g, 14.58 mmol). DIPEA (3.76 g, 29.09 mmol) in THF (4 g) was added to the resulting solution while maintaining an internal temperature of –6 to –4° C. The resulting mixture was stirred at –6 to –4° C. for 1 h and allowed to warm to 20 to 25° C. over 3 h then stirred at this temperature overnight. THF was removed in vacuo at 35-40° C. and the remaining mixture was diluted with MeOH (20 g). This resulting yellow solution was added dropwise, over 5-10 min, to a cooled solution of Na$_2$CO$_3$ (3.34 g) in H$_2$O (330 g) and rinsed with MeOH (5 g). The resulting mixture was stirred for 15 min and the precipitate was collected by filtration. This crude solid was suspended in acetonitrile (110 g), warmed to 60-70° C., and the fine suspension was added to water (48 g) and cooled to 20-25° C. The resulting solid was separated, rinsed with a solution of H$_2$O (24 g) and acetonitrile (28 g) and dried under vacuum at 38-42° C. to give Boc-LLK(Z)LL*LLK(Z)

LLLLK(Z)-LLLLK(Z)—OBzl (SEQ. ID No. 3) (12.05 g, 89%), D-8 (*) diastereomer: 5.5%.

Step 17

(SEQ. ID No. 3)
H-LLK(Z)LLLLK(Z)LLLLK(Z)-LLLLK(Z)-OBzI•TFA

Trifluoroacetic acid (180 g) was cooled to −10 to −14° C. The powdered solid Boc-LLK(Z)LLLLK(Z)LLLLK(Z) LLLLK(Z)—OBzl (SEQ. ID No. 3) (50 g, 17.6 mmol) was added slowly into the cooled TFA. The mixture stirred at −9 to −5° C. for 3 h or until complete dissolution. Ethanol (99 g) was added slowly at −9 to −5° C. The resulting cold solution was added slowly to a solution of $KHCO_3$ (197.5 g, 507 mmol) in water (750 g) cooled to 12-18° C. The white solid was collected by filtration and washed with water (480 g). The wet solid was slurried in water (500 g) for 10 min then filtered and washed with water (50 g). The white solid was dried under reduced pressure at 40-45° C. to give H-LLK(Z) LLLLK(Z)LLLLK(Z)-LLLLK(Z)—OBzl_.TFA (SEQ. ID No. 3) (51.16 g, 102%), HPLC purity: 88.2%.

Step 18

(SEQ. ID No. 1)
Z-K(Z)LLLLK(Z)LLLLK(Z)LLLLK(Z)-LLLLK(Z)-OBzI

Finely powdered H-LLK(Z)LLLLK(Z)LLLLK(Z) LLLLK(Z)—OBzl.TFA (SEQ. ID No. 3) (23.13 g, 8.1 mmol) was added slowly to a mixture of NMP (40 g) and THF (160 g). This was followed by the addition of Z—K(Z)LL-OH (5.71 g, 8.9 mmol). The resulting solution was cooled to −3 to 3° C. HOOBt (3.96 g, 24.3 mmol) and HBTU (3.99 g, 10.5 mmol) were added followed by NMP (for rinse) and the mixture stirred for a few minutes until complete dissolution then cooled to −6 to −9° C. A solution of DIPEA (4.19 g, 32.4 mmol) in THF (4 g) was added slowly at −6 to −9° C. leading to a deep orange color. The solution was stirred for 2 h at −6 to −9° C., for 3 h at −1 to 3° C. and then was warmed up slowly to room temperature. The THF was distilled under reduced pressure at 40-45° C. to give an oily yellow residue. The residue was added to a solution of $Na_2CO_3$ (1.8 g) at 15-25° C. The resulting suspension was stirred for 15 min and the solid was isolated by filtration and washed with water (75 g) then with a mixture of water (26 g) and iPrOH (32 g). The wet crude solid was slurried in a mixture of iPrOH (104 g) and water (86 g) for 30 min at 20-25° C. The solid was collected by filtration, washed with a mixture of iPrOH (27 g) and water (22 g) and dried in vacuo at 38-42° C. to give Z—K(Z) LL*LLK(Z)LLLLK(Z)-LLLLK(Z)-LLLLK(Z)—OBzl (SEQ. ID No. 1) (25.1 g, 92%), HPLC purity: 90%, D-3 (*) diastereomer: 1.1%.

Step 19

(Lys-Leu$_4$)$_4$-Lys (SEQ. ID No. 1)

Z—K(Z)LLLLK(Z)LLLLK(Z)LLLLK(Z)-LLLLK(Z)—OBzl (SEQ. ID No. 1) (630 g, 187.26 mmol) was added to a mixture of trifluoroacetic acid (2815 g) and acetic acid (3969 g). After dissolution, water (630 g) was added followed by wet (50% $H_2O$) 5% Pd/C (252 g). The mixture was hydrogenated under a $H_2$ pressure of about 2.8 bar for 3 h. The mixture was filtered in absence of air and was rinsed with a mixture of TFA (939 g), AcOH (1323 g) and $H_2O$ (210 g). The filtrate was concentrated at <35° C. under reduced pressure to give an oil. This oil was dissolved in iPrOH (2021 g) and added dropwise, within 30 min into stirred t-butyl methyl ether (12405 g) and rinsed with iPrOH (300 g). After stirring for 30 min at rt, the solid was collected by filtration and was washed, immediately with t-butyl methyl ether (18173 g) and dried in a vacuum oven at <40° C. to give crude (Lys-Leu$_4$)$_4$-Lys. (SEQ. ID No. 1) Yield: 534 g, 94.7%, HPLC area % purity: 81.8%.

EXAMPLE 2

Step 1

Boc-Lys(Z)-Leu-Leu-OH

Boc-Lys(Z)-Leu-Leu-OMe (12.0 g, 19.33 mmol) was dissolved in acetone (41.0 g, 52 mL) at 22-23° C. A solution of NaOH (1.94 g, 48.5 mmol) in water (18.0 g) was added over 5 min. After stirring for 40 min., the reaction was quenched with a solution of citric acid (10.2 g, 53.0 mmol) in water (18.0 g). The acetone was removed on a rotary evaporator at 40° C. The remaining mixture was extracted with ethyl acetate (2×65 mL). The EtOAc extract was washed with water (50 g) then with aqueous saturated sodium chloride solution (50 g). The EtOAc extract was dried over anhydrous $MgSO_4$ (10 g). The EtOAc solution was filtered and diluted with DMF (40. g). The ethyl acetate was evaporated at 40° C. under reduced pressure to give the solution of the product in DMF. Weight of solution ~52 g.

Step 2

H-Leu-Leu-Lys(Z)-Leu-Leu-OMe•HCl (SEQ. ID No. 2)

Boc-Leu-Leu-Lys(Z)-Leu-Leu-OMe (SEQ. ID No. 2) (18.2 g, 21.5 mmol) was added to a solution of HCl gas (31.0 g, 850 mmol) in MeOH (360 g) and cooled to 5° C. The reaction mixture was stirred, allowed to warm up to room temperature and stirring was continued for 4.5 h. The reaction mixture was cooled to 0° C., poured into ice/$H_2O$ (630 g) and stirred for 1 h. The white solid was collected by filtration, washed with distilled water (500 mL) and air dried. Yield of product: 14.8 g, 87.6%; HPLC area % purity: 99.2%.

Step 3

(SEQ. ID No. 4)
Boc-Lys(Z)-Leu-Leu-Leu-Leu-Lys(Z)-Leu-Leu-OMe

H-Leu-Leu-Lys(Z)-Leu-Leu-OMe.HCl (SEQ. ID No. 2) (15.12 g, 19.33 mmol) was dissolved in DMF (100 g). A solution of 11.73 g Boc-Lys(Z)-Leu-Leu-OH (19.33 mmol) in DMF (obtained from step 20) was added and the resulting solution was cooled to −5° C. while stirring under nitrogen. To the cold solution was added HOOBt (3.30 g, 20.2 mmol) followed by HBTU (7.67 g, 20.2 mmol) and DIPEA (7.76 g, 60.03 mmol) over 5 min. The clear yellow solution became cloudy after about 5 min. The reaction mixture stirred at −4° C. for 80 min. The mixture became thicker as the reaction progressed but was easy to stir. The mixture was quenched by adding a solution of K₂CO₃ (10.0 g) in water (200 g). The mixture warmed up gently on a steam bath to 40-45° C. and was kept at that temperature for about 30 min. The solid was collected by filtration and washed with hot (60-70° C.) water (2×150 g). The product was dried overnight in a vacuum oven at 40° C. to give Boc-Lys(Z)-Leu₄Lys(Z)-Leu-Leu-OMe (SEQ. ID No. 4) (25.0 g, 96.8%). HPLC area % purity: 94%.

Step 4

(SEQ. ID No. 4)
Boc-Lys(Z)-Leu-Leu-Leu-Leu-Lys(Z)-Leu-Leu-OH

Boc-Lys(Z)-Leu₄Lys(Z)-Leu-Leu-OMe (SEQ. ID No. 4) (16.03 g, 12.0 mmol) was powdered and suspended in THF (240.0 g, 270 mL). The mixture stirred and cooled to −4° C. under nitrogen. The cold solution was treated with 40% aqueous tetrabutylammonium hydroxide (24.0 g, 37.0 mmol), added dropwise over 5 min. (the temperature maintained at <−1° C. during the addition). The suspension dissolved to form a clear light yellow solution. The HPLC analysis indicated a complete hydrolysis after 50 min. The reaction mixture stirred at −2° C. for 70 min. and was quenched with a solution of glacial acetic acid (6.0 g, 100.0 mmol) in water (9.0 g). The reaction mixture remained as a clear solution. The reaction flask was equipped with an addition funnel containing an aqueous solution made of saturated aqueous sodium chloride (50.0 g) and water (200 g). The initial volume of the solution in the reaction flask was marked. The reaction mixture was heated to distill the THF at atmospheric pressure while adding aqueous NaCl to maintain a constant volume. Precipitation started about midway of the evaporation/addition. Near the end of evaporation foaming occurred. At that point, heating stopped and the remaining aqueous solution was added. The temperature reached 83° C. at the end of evaporation and a total of 224 g of THF distillate was collected. The hot mixture was centrifuged to collect the white solid product. The solid was washed with a total of hot (50° C.) water (200 g). The white solid was dried at 40° C. in a vacuum oven to give Boc-Lys(Z)-Leu-Leu*-Leu-Leu-Lys(Z)-Leu-Leu**—OH (SEQ. ID No. 4) (15.6 g, 98%), HPLC area % purity: 91.4%. diastereomeric purity: 99.08%, D3-diastereomer(*): 0.42%, D8-diastereomer(**): 0.50%.

Step 5

Boc-(Lys(Z)-Leu₄)₄Lys(Z)-OBzl    (SEQ. ID No. 1)

Boc-K(Z)LLLLK(Z)LL-OH (SEQ. ID No. 4) (6.61 g, 5.0 mmol) was mixed with H-LLK(Z)LLLLK(Z)-LLLLK(Z)—OBzl.HCl (SEQ. ID No. 5) (10.32 g, 5.0 mmol) and 85% Bu₄NCl (7.5 g, 22.9 mmol) in tetrahydrofuran (400 g) and purified water (30 g). The mixture was cooled to 0° C. and treated with HOOBt (2.25 g, 15.0 mmol) and N,N-diisopropylcarbodiimide (DIC) (1.90 g, 15.0 mmol), followed by N,N-diisopropyl ethylamine (DIPEA) (2.25 g, 17.4 mmol). The yellow solution was stirred at 0° C. for 1 h then at rt (23-25° C.) for 20 h and finally at 30° C. for 2 h. The reaction mixture became a clear yellow solution in a few hours from the start of reaction. At the end of the 24 h period, the yellow solution was diluted with 1-methyl-2-pyrrolidone (100 g) and the THF was evaporated at 35-40° C. under reduced pressure. The residual solution was added to cold water (350 g) containing potassium carbonate (12 g). The flask was rinsed with methanol (50 mL) and the rinse was combined with the aqueous mixture. The product precipitated as a fine yellow solid. The mixture stirred slowly at rt for 20-30 min and the solid was collected by filtration and was washed with water (150 mL) followed by an 80:20 MeOH/H₂O mixture (250 mL). The solid was air-dried on the filtration funnel for about an hour then further dried in a vacuum oven at 40° C. overnight. The product was a light yellow solid, 16.6 g (99.7%), HPLC area % purity: 92%.

Step 6

(Lys-Leu₄)₄Lys    (SEQ. ID No. 1)

Boc-(Lys(Z)-Leu₄)₄Lys(Z)—OBzl (SEQ. ID No. 1) (16.0 g, 4.8 mmol) was dissolved in trifluoroacetic acid (64.0 g) at room temperature. It took about 20-25 min for the solid to completely dissolve. Glacial acetic acid (80.0 g) was added followed by distilled water (16.0 g) and finally 5% palladium on moist activated carbon (4.5 g). The mixture was hydrogenated at 40-50 psi overnight (about 18 h). The resulting mixture was filtered through a Buchner funnel (5.5 cm diameter) using five Whatmann qualitative filter papers. The hydrogenation flask was rinsed with trifluoroacetic acid (10.0 g). The colorless filtrate was concentrated under reduced pressure at 40-45° C. to a weight of about 30 g. The residue was dissolved in trifluoroacetic acid (74.0 g) and was added slowly over 10 min to t-butyl methyl ether (300 mL) while cooling in an ice bath with stirring. The product precipitated as a white solid. After stirring for about 15 min., the product was collected by filtration and was washed immediately with t-butyl methyl ether (100 mL). The solid was dried in a vacuum oven at 40° C. overnight. Yield of isolated solid: 14.74 g (95.6% assuming the formation of a hexatrifluoroacetate salt), HPLC area % purity: 80.5%.

EXAMPLE 3

Ac-D-Nal-D-p-Cal-OH

Ac-D-Nal-D-p-Cal-OMe (45.3 g, 100.0 mmol), powdered to a fine solid, was suspended and stirred in THF (450.0 mL) then cooled to −6° C. The cold suspension was treated with 40% aqueous tetrabutyl ammonium hydroxide (72.0 g, 111.0 mmol), added in such a rate that the reaction temperature did not exceed −3° C. The solid dissolved as the base was added and was a completely in solution at the end of addition. The reaction was complete shortly after the end of addition (as determined by HPLC analysis). The reaction was acidified at −6° C. by a slow addition of a solution of conc. HCl (20 mL) in water (20 mL). After acidification, the clear solution was diluted with water (100 mL) and most of the THF was evaporated on a rotovap at 25-30° C. until heavy precipitation occurred. The mixture was diluted with methanol (200 mL) and the solid was collected by filtration. The flask and the solid were rinsed with additional methanol (150 mL) and the solid was air-dried. Yield of isolated dry solid: 40.2 g, 91.6%. HPLC area % purity: 93.7%, diastereomer (*): 2.6%, Ac-D-Nal-D-p-Cal*-OH

EXAMPLE 4

Ac-D-Nal-D-pCal-D-3-Pal-L-Ser(OH)-OH (SEQ. ID No. 7)

Ac-D-Nal-D-p-Cal-D-3-Pal-L-Ser (OH)—OBzl (SEQ. ID No. 7) (58.1 g, 76.0 mmol), powdered to a fine solid, was suspended in THF (400.0 mL) then stirred and cooled to −5° C. The cold suspension was treated with 40% aqueous tetrabutylammonium hydroxide (98.6 g, 152.0 mmol), added in such a rate that the reaction temperature did not exceed −2° C. (about 15 min). The solid dissolved slowly after the base was added and completely dissolved after 40 min following the end of addition. The reaction mixture stirred for a total of 1.5 h, during which the temperature was allowed reach and remain at 0° C. The HPLC analysis indicated a complete hydrolysis. The resulting clear solution was poured into a solution of glacial acetic acid (35 g) in ice/water (1.1 L) with stirring. The product precipitated as a thick white solid which was collected by filtration. The wet cake was slurried in hot (65° C.) water (1 L) and filtered. The wet cake was slurried in methanol (700 mL) and heated to boiling with stirring. The solid was collected by filtration from the hot slurry and was rinsed with methanol (150 mL) then was air-dried. Yield of isolated dry powdered solid: 44.8 g, 87.4%. HPLC area % analysis of product: 95%, diastereomer (*): 1.7%, Ac-D-Nal-D-p-Cal-D-3-Pal-L-Ser*(OH)—OH. (SEQ. ID No. 7)

---

What is claimed is:

1. A liquid phase method of deprotecting a peptide's ester protected carboxy group having an α chiral center which consists of reacting said peptide ester with a tetraalkylammonium hydroxide and water in an inert organic solvent at a low temperature to form the deprotected peptide's carboxy group.

2. The method of claim 1 wherein, the tetraalkylammonium hydroxide is tetrabutylammonium hydroxide, the inert organic solvent is DMF or THF and the temperature is about −20 to 0 C.

* * * * *

SEQUENCE LISTING

```
<160> NUMBER OF SEQ ID NOS: 7

<210> SEQ ID NO 1
<211> LENGTH: 21
<212> TYPE: PRT
<213> ORGANISM: Artificial Sequence
<220> FEATURE:
<223> OTHER INFORMATION: Each molecule is prepared through chemical
      reactions.

<400> SEQUENCE: 1

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 2
<211> LENGTH: 5
<212> TYPE: PRT
<213> ORGANISM: Artificial Sequence
<220> FEATURE:
<223> OTHER INFORMATION: Each molecule is prepared through chemical
      reactions.

<400> SEQUENCE: 2

Leu Leu Lys Leu Leu
1               5

<210> SEQ ID NO 3
<211> LENGTH: 16
<212> TYPE: PRT
<213> ORGANISM: Artificial Sequence
<220> FEATURE:
<223> OTHER INFORMATION: Each molecule is prepared through chemical
      reactions.

<400> SEQUENCE: 3

Leu Leu Lys Leu Leu Leu Leu Lys Leu Leu Leu Leu Lys Leu Leu Leu
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: Each molecule is prepared through chemical
      reactions.

<400> SEQUENCE: 4

Lys Leu Leu Leu Leu Lys Leu Leu
```

```
<210> SEQ ID NO 5
<211> LENGTH: 13
<212> TYPE: PRT
<213> ORGANISM: Artificial Sequence
<220> FEATURE:
<223> OTHER INFORMATION: Each molecule is prepared through chemical
      reactions.

<400> SEQUENCE: 5

Leu Leu Lys Leu Leu Leu Leu Lys Leu Leu Leu Leu Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Each molecule is prepared through chemical
      reactions.

<400> SEQUENCE: 6

Leu Leu Lys Leu Leu Leu Leu Lys
1               5

<210> SEQ ID NO 7
<211> LENGTH: 4
<212> TYPE: PRT
<213> ORGANISM: Artificial Sequence
<220> FEATURE:
<223> OTHER INFORMATION: Each molecule is prepared through chemical
      reactions.
<220> FEATURE:
<221> NAME/KEY: misc_feature
<222> LOCATION: (1)..(3)
<223> OTHER INFORMATION: Xaa can be any naturally occurring amino acid

<400> SEQUENCE: 7

Xaa Xaa Xaa Ser
1
```